US006331405B1

(12) United States Patent
Rambukkana et al.

(10) Patent No.: US 6,331,405 B1
(45) Date of Patent: Dec. 18, 2001

(54) **RECEPTOR FOR *MYCOBACTERIUM LEPRAE* AND METHODS OF USE THEREOF**

(75) Inventors: Anura Rambukkana, New York; Vincent A. Fischetti, West Hempstead, both of NY (US); Kevin P. Campbell, Iowa City, IA (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/209,108

(22) Filed: Dec. 10, 1998

(51) Int. Cl.[7] ............................. G01N 33/53; C12N 1/20; C12Q 1/02
(52) U.S. Cl. ............................. 435/7.2; 435/4; 435/7.1; 435/7.32; 435/7.8; 435/29; 435/253.1
(58) Field of Search ................................. 435/4, 7.2, 7.21, 435/7.32, 7.8, 69.1, 368, 253.1, 317.1, 29, 7.1; 800/3, 9, 13

(56) References Cited

U.S. PATENT DOCUMENTS 5,580,859 * 12/1996 Felgner et al. ........................ 514/44

OTHER PUBLICATIONS

A. Rambukkanaa, Trends in Microbiology, 8:23–28, 2000.*
Rambukkana et al., Science, 282:2076–2078, 1998.*
Rosenberg et al., Science, 287:175, 2000.*
Alderete et al., Methods In Enzymology, 236:318–333, 1994.*
Verma et al., Nature, 387–239–242, 1997.*
Ledley, Pharmaceutical Research, 13:1595–1614, 1996.*
Branch, TIBS, 23:45–50, 1998.*
Agrawal, TIBTECH, 14:376–387, 1996.*
Whitelaw et al., Transgenic Research, 1:3–13, 1991.*
Wall, Theriogenology, 45:57–68, 1996.*
Bradley et al., Bio/Technology, 10:534–539, 1992.*
Palmiter et al., Ann. Rev. Genet., 20:465–499, 1986.*
Colman, Am. J. Clin. Nutr., 63:639S–45S, 1996.*
Palmiter et al., Proc. Natl. Acad. Sci., 88:478–482, 1991.*
Strojek et al., Genetic Engineering: Principles and Methods, Plenum Press, 10:221–246, 1988.*
Pursel et al., J. Reprod. Fert., Suppl. 40:235–245, 1990.*
Houdebine et al., J. Biotechnology, 34:269–287, 1994.*

Orkin et al., in Report And Recommendations Of The Panel To Assess The NIH Investment In Research On Gene Therapy, Dec. 7, 1995.*
Durbeej et al., Curr. Opin. Cell Biol. 10:594 (1998).
Finlay and Cossart, Science 276:718 (1997).
Cohen et al., J. Cell Biol. 136:1047 (1997).
Williamson et al., Hum. Mol. Genet. 6:831 (1997).
Rambukkana et al., Cell 88:811–21 (1997).
Yamada et al., J. Neurochem. 66:1518 (1996).
Yamada et al., J. Biol. Chem. 271:23418 91996).
Mercurio, Trends Cell Biol. 5:419 (1995).
Yang et al., J. Biol. Chem. 270:11711 (1995).
Durbeej et al., J. Cell Biol. 130:79 (1995).
Campbell, Cell 80:675 (1995).
Wkly. Epidemiol. Rec. 70:269 (1995).
Schorey et al., Infect. Immun. 63:2652 (1995).
Burgeson et al., Matrix Biol. 14:209 (1994).
Yamada et al., FEBS Lett. 352:49 (1994).
Sunada et al., J. Biol. Chem. 269:13729 (1994).
Gee et al., Cell 77:675 (1994).
Suzuki et al., Eur J. Biochem. 220:283 (1994).
Timpl and Brown, Matrix Biol. 14:275 (1994).
Anton et al., Dev. Biol. 164:133 (1994).
Ervasti and Campbell, J. Cell Biol. 122:809 (1993).
Yurchenco et al., J. Biol. Chem. 268:8356 (1993).
Einheber et al., J. Cell Biol. 123:1223 (1993).
Jaakkola et al., J. Neurocytol. 22:215 (1993).
Engvall et al., Exp. Cell Res. 198:115 (1992).
Ibraghimov–Beskrovnaya et al., Nature 355:696 (1992).
Falkow, Cell 65:1099 (1991).
Ervasti and Campbell, Cell 66:1121 (1991).
Ervasti et al., J. Biol. Chem. 266:9161 (1991).
Sanes et al., J. Cell Biol. 111:1685 (1990).
Job, Int. J. Lepr. 57:532 (1989).
Cornbrooks et al., Proc. Natl. Acad. Sci. USA 80:3850 (1983).

* cited by examiner

Primary Examiner—Deborah J. R. Clark
Assistant Examiner—Janet M Kerr
(74) Attorney, Agent, or Firm—Darby & Darby

(57) ABSTRACT

The present invention relates to the discovery that the α-dystroglycan receptor is required for *Mycobacterium leprae* entry into cells, assays for high throughput screening of drugs for use in treatments against leprosy, and methods for studying the role of the receptor in neurodegenerative and musculodegenerative diseases, and the like.

8 Claims, 8 Drawing Sheets

α-dystroglycan
Rat Schwann cells

α-dystroglycan
Human Schwann cells

RECEPTOR FOR *MYCOBACTERIUM LEPRAE* AND METHODS OF USE THEREOF

The research that led to the present invention was supported in part by Grant No. AIU522 from the National Institutes of Health. Accordingly, the United States Government has certain rights to this invention.

FIELD OF THE INVENTION

The present invention relates to the discovery that the α-dystroglycan receptor is required for *Mycobaeferium leprae* entry into cells, assay for high throughput screening of drugs for use in treatments against leprosy, and methods for studying the role of the receptor in neurodegenerative and musculodegenerative diseases, and the like.

BACKGROUND OF THE INVENTION

*M. leprae* Binding to Target Cells

Pathogenic bacteria are adapted to exploit a variety of host cell functions, and host cell receptors usually serve as the initial target for bacterial interaction with a specific cell type (Finlay and Cossart, Science 276:718, 1997; Falkow, Cell 65:1099, 1991). However, not much is known about the bacterial receptors in the nervous system and how bacteria interfere with these neuronal cell receptor-associated functions. *Mycobacterium leprae*, the causative organism of leprosy, is an intracellular pathogen which invades the Schwann cell of the peripheral nervous system (Falkow, supra). The neural tropism of this disease has been recognized for almost 150 years but has remained unexplained. At present, it is estimated that 2–3 million leprosy patients in the world are physically disabled as a result of damage to peripheral nerves and the attendant sensorimotor loss (Job, Int. J. Lpr. 57:532, 1989; Noordeen et al., Bull. World Health Org. 70:7, 1992).

During infection, *M. leprae* cause significant damage to peripheral nerves leaving patients with disabilities and deformities (Job, supra). Schwann cells are unable to destroy the pathogens that reside intracellularly, and access of therapeutic agents to this site is limited owing to the blood-nerve barrier. Although antibiotic therapy and long-term multidrug treatment are effective bacteriological cures for leprosy, they do not reverse the nerve function loss in these patients (WHO Weekly Epidemiological Record. Sep. 20, p. 269, 1995). Understanding the mechanisms of *M. leprae*-Schwann cell interaction may yield new therapeutic strategies for the prevention of nerve damage.

In the endoneurium of peripheral nerves, all Schwann cells are characterized by a basal lamina covering. Since *M. leprae* must interact with the basal lamina in order to reach the Schwann cell, tropism to this site and perhaps cellular entry might involve the components of Schwann cell basal lamina. Schwann cell basal lamina is comprised of laminin, type IV collagen, entactin/nidogen, and heparin sulfate proteoglycans (Combrooks et al., Proc. Natl. Acad. Sci. USA 80:3850, 1983; Jaakkola et al., J. Neurocytol. 22:215, 1989; Sanes et al., J. Cell Biol. 111:1685, 1990). Although there is evidence that *M. leprae* binds to fibronectin (Schorey et al., Infect. Immun. 63:2652, 1995), this binding may not be relevant for *M. leprae* interaction with Schwann cells in vivo, since both fibronectin mRNA and protein are absent in Schwann cell basal lamina in situ and in primary cultures (Combrooks et al., 1983, supra; Jaakkola et al., 1989, supra). Conversely, considering the continuous presence of laminin around the Schwann cell-axon unit in vivo, laminin appeared to be a candidate as an initial target for *M. leprae*.

Laminins (LNs) are glycoproteins comprised of three polypeptide chains, α, β, and γ. The α chain distinguishes itself by having an extra domain at the C-terminus, i.e., the G domain (Burgeson, et al., Matrix Biol. 14:209, 1994; Timpl and Brown, Matrix Biol. 14:275, 1994). At least 10 genetically distinct LN chains have been identified ($\alpha1$, $\alpha2$, $\alpha3$, $\alpha4$, $\alpha5$, $\beta1$, $\beta2$, $\beta3$, $\gamma1$, and $\gamma2$), which assemble into 11 different LN isoforms (LN-1 to -11), each with restricted tissue distribution (reviewed in Timpl and Brown, supra Engvall and Wewer, J. Cell Biochem. 61:493, 1996). In the Schwann cell basal lamina, the predominant LN variant is LN-2 (merosin), which comprises tissue-specific α2 heavy chain together with the β1 and γ1 light chains (Leivo and Engvall, Proc. Natl. Acad. Sci. USA 85:1544, 1988; Engvall et al., Cell Regul. 1:731, 1990. LN-2 not only forms a major basement membrane network, but also enables a variety of functions of neural cells (Engvall et al., Exp. Cell Res. 198:115–123 1992; Yurchenco et al., J. Biol. Chem. 268:8356, 1992; Anton et al., Dev. Biol. 164:133, 1994). The major cell receptors for LN are the members of the integrin superfamily (Mercurio, Trends Cell Biol. 5:419, 1995). Several integrin receptors bind to LN, and $\alpha_6\beta_1$ and $\alpha_6\beta_4$ integrins, particularly the $\beta_4$ subunit, appear to be involved in the Schwann cell interaction with LN (Einheber et al., J. Cell Biol. 123:1223, 1993; Jaakkola et al., supra; Feltri et al., Development 120:1287, 1994; Niessen et al., Development 120:1287, 1994).

The neural tropism of *M. leprae* involves the bacterial binding to the G domain of the LN-α2 chain, which serves as a bridge between *M. leprae* and the native LN receptors on Schwann cells (Rambukkana et al., Cell 88:811, 1997). The LN-α2G domain serves as both the bacterial and human cell binding site, which is possibly mediated by the $\beta_4$ integrin subunit as a host-cell receptor for LN-α2G-mediated *M. leprae* cell interaction. However, the actual host cell receptor had not been identified. In order to provide more effective treatments for leprosy, and to better understand this disease and other musculo- and neurodegenerative diseases involving laminins, it is necessary to determine the host cell receptor.

Dystroglicans

Dystroglycan, a component of the dystrophin-glycoprotein complex, is a laminin receptor encoded by a single gene and cleaved into two proteins, peripheral membrane α-dystroglycan and transmembrane β-dystroglycan, by post-translational processing (Ibraghimov-Beskrovnaya et al., Nature 355:696, 1992; Ervasti and Campbell, Cell 66:1121, 1991; Campbell, Cell 80:675, 1995). While α-dystroglycan interacts with laminin-2 in the basal lamina of Schwann cells, β-dystroglycan appears to bind to dystrophin-containing cytoskeletal proteins in muscles and peripheral nerves (Ervasti and Campbell, J. Cell. Biol. 122:809, 1993: Suzuki et al., Eur. J. Biochem. 220:283, 1994; Yamada et al., J. Neurochem. 66:1518, 1996; Yang et al., J. Biol. Chem. 270:11711, 1995). Dystroglycan is involved in the formation of neuromuscular junctions in the morphogenesis early development and in the pathogenesis of muscular dystrophies (Gee et al., Cell 77:675, 1994; Durbeej et al., J. Cell. Biol. 130:79, 1995; Williamson et al., Hum. Mol. Genet. 6:831, 1997; Campbell, supra). Loss or a defect of laminin-2-α-dystroglycan interaction causes certain types of muscular dystrophies and peripheral neuropathies (Sunada et al., J. Biol. Chem. 269:13729, 1994).

As noted above, in peripheral nerves, α-dystroglycan appears to link extracellular laminin-2 to the intracellular cytoskeleton through β-dystroglycan and associated proteins. In addition to playing a structural role, this system also regulates host cell functions (Campbell, supra; Ervasti and Campbell, 1993, supra, Suzuki et al., supra; Yang et al., supra).

There is a need in the art to identify a cell receptor involved in M. leprae infectivity and invasion. There is a further need to identify a laminin-receptor that mediates M. leprae invasion. The present invention addresses this need by identifying the sought-after receptor. This discovery has unexpected and surprising implications, as elaborated below.

SUMMARY OF THE INVENTION

The present invention advantageously provides a method for identifying a compound that inhibits binding of M. leprae to an α-dystroglycan polypeptide. The method comprises detection of inhibition of M. leprae to α-dystroglycan in the presence of a test compound. A molecule comprising the laminin-2G-domain is present to mediate the binding.

In a further embodiment the invention provides a method of inhibiting binding of M. leprae to a cell. This method comprises administering an inhibitory amount of a compound that inhibits binding or antisense DNA corresponding to an α-dystroglycan gene to the cell, whereby the level of expression of α-dystroglycan by the cell is reduced.

In another embodiment the invention provides a method for identifying a component of M. leprae involved in its binding to a cell comprising the step of detecting binding of a component isolated from M. leprae to α-dystroglycan.

In yet another embodiment the invention provides a method for identifying a gene whose expression is regulated in response to binding of M. leprae to the cell, wherein the cell expresses α-DG, comprising performing a gene expression evaluation assay after binding of M. leprae to α-DG in the presence of LNα2G to the cell to identify the gene whose expression is regulated by binding of M. leprae-LNα2 to the cell.

In still another embodiment the invention provides a composition comprising a mycobacterium, a molecule comprising a laminin α-2G domain, and an α-DG polypeptide, wherein the α-DG polypeptide is isolated.

In addition, the invention provides a composition comprising a mycobacterium, a molecule comprising a laminin α-2G domain, and an α-DG polypeptide, wherein the α-DG is expressed in a cell that does not endogenously express α-DG.

The invention further provides a transgenic, non-human animal that expresses dystroglycan, which can be used as a model for leprosy. Optimally, the transgenic animal is infected with M. leprae.

DETAILED DESCRIPTION OF THE INVENTION

Figure 1A:
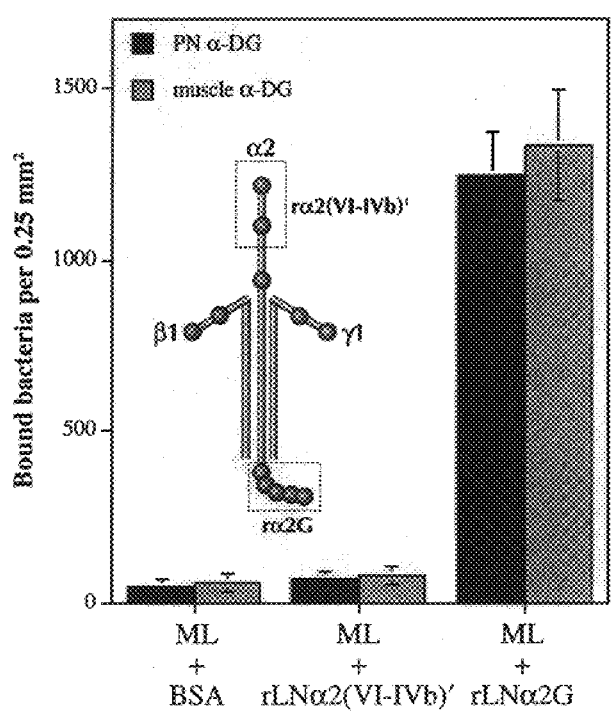
FIGS. 1A and 1B. (A) Schematic diagram showing binding of M. leprae to α-dystroglycan purified from bovine peripheral nerve or muscle cells in the presence or absence of the G domain of laminin-α2 chain. Inset: laminin-α2 molecule showing the location of the NH2-terminal (VI-IVb)' fragment and the COOH-terminal G domain of α2 chain. (B) Coomassie blue stained SDS-PAGE showing purified native α-dystroglycan preparations and recombinant laminin-α2 chain fragments used in Example 1 (peripheral nerve α-dystroglycan (PNα-DG; 120-kD), muscle α-dystroglycan (muscle α-DG; 156-kD), rLN-α2 (VI-IVb)' (116-kD) and rLN-α2G (120-kD)).

The present invention is based on the surprising discovery of a novel receptor-ligand interaction that mediates the interaction of M. leprae, the causative organism of leprosy, to Schwann cells. Specifically, α-dystroglycan (α-DG), which is part of dystroglycan, a receptor present, inter alia, on Schwann cells, has been unexpectedly found to interact with M. leprae. The interaction of M. leprae and α-DG is mediated by the G-domain of the α-2 chain of laminin-2. Other fragments of the laminin-α2 chain do not mediate binding of the bacteria to the receptor. Addition of free α-DG inhibits the laminin-2-mediated binding of *M. leprae* to Schwann cells. Thus, there are at least two binding sites on LN-α2G for *M. leprae* and α-DG (discussed in the Examples, infra).

In general, *M. leprae* binds to laminin-2 which, in turn, binds to α-dystroglycan on Schwann cells. α-Dystroglycan assists with entry of the bacteria into the cell. This phenomenon is exploited by the present invention to determine other roles of α-dystroglycan in leprosy and other diseases involving this receptor. For instance, loss or defect of laminin-2-α-dystroglycan interaction is associated with muscular dystrophy and peripheral neuropathies, indicating a role for α-dystroglycan in these diseases. The present invention provides for methods of determining the role of α-dystroglycan in the pathogenicity of *M. leprae* as a causative agent of leprosy. Furthermore, various assays described herein can be used to determine the role of α-dystroglycan in other diseases associated with this receptor.

These findings of the invention permit further exploration and understanding of the role of α-DG in the uptake of *M. leprae* into Schwann cells, identification of adhesins of *M. leprae* involved in its uptake, and identification of drugs and factors that inhibit binding of *M. leprae* to Schwann cells for use in treatments of leprosy. The findings of the invention can also be exploited to ascertain the role of the α-DG and LN-α2G interaction (LN-2-α-DG) in other diseases, such as muscular dystrophy, where there is loss or deficiency in α-DG function.

As used herein, the term "isolated" means that the referenced material is removed from the natural environment in which it is normally found. In particular, isolated biological material is free of cellular components. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate unrelated materials, i.e., contaminants. For example, a purified protein is preferably free of other proteins or nucleic acids with which it is associated in a cell.

In a specific embodiment, the term "about" or "approximately" means within 20%, preferably within 10%, and more preferably within 5% of a given value or range.

*Mycobacterium leprae*

*M. leprae* used in the present invention can be obtained through laboratories funded and authorized by the National Institutes of Health to distribute the bacterium. For example, *M. leprae* can be obtained under this program from the laboratory of Dr. Patrick Brennen at the Colorado State University. As used herein, the term "mycobacterium" and any grammatical variants thereof refer to *M. leprae*.

Any means known in the art to isolate and culture *M. leprae* can be used. It is possible to obtain tissue samples from infected individuals, and to isolate the bacterium from leprous nodules found in these samples (Murohashi and Yoshida, Acta Leprol. 10:3–21, 1978; see also Kato and Ishaque, Int. J. Lepr. Other Mycobact. Dis. 44:431–4, 1976), or from lymph (Sanabria et al., Rev. Cubana Med. Trop. 33:13–8, 1981). Leprous nodules can be preserved by freezing to supply primary myobacterial cultures (Murohashi and Yoshida, supra). Alternatively, samples cultured in armadillos can be isolated (Matsuo et al., Repura 45:63–7, 1977). These and other isolation techniques are known in the art, and can be used in the practice of the invention, if mycobacterium samples become unavailable from the NIH laboratories, or if it is desired to use other mycobacterium strains for evaluation and testing, as described herein.

Indeed, any strain of *M. leprae* can be used in the practice of the present invention. Different strains may demonstrate different degrees of specificity for the binding interaction with α-DG disclosed herein. It may be possible, as well, to identify isolate strains that do not interact with α-DG.

Various methods for culturing mycobacteria in vivo and in vitro are known as well (e.g., Nakamura, Int J Lepr Other Mycobact Dis 63:28–34, 1995). As noted above, armadillos are known for their ability to propagate viable *M. leprae* (Matsuo et al., supra). Alternatively, in vitro techniques, such as cultivation on hyaluronic acid based medium (Kato and Ishaque, supra; Skinsnes et al., Int. J. Lepr. Other Mycobact. Dis. 43:193–203, 1975) can be used. Mycobacterial cultivation has been reviewed (Pattyn, Lepr. India 49:80–95, 1977).

α-Dystroglycan and Dystroglycan

As used herein the term α-DG refers to the laminin receptor that is a component of the dystrophin-glycoprotein complex. It is part of a heterodimer comprising β-dystroglycan; the former binds to the extracellular matrix, the latter is a transmembrane protein that binds to the cytoskeletal protein dystrophin. The two polypeptides are expressed from a single gene as a pro-protein, which is cleaved during post-translational processing. Thus, when the specification speaks about expression of α-DG, it is generally intended that the entire dystroglycan pro-protein is expressed. However, it is also possible to clone and express the region of the dystroglycan gene encoding the α-DG polypeptide, if that is desired. Cloning and expression of α-DG polypeptide can be useful to mycobacterial binding to target cells, as discussed below.

Dystroglycan has been found in several species, including human, rabbit, mouse, cat, cow, pig, and *Torpedo californica*, and is highly conserved between species. Thus, as used herein, dystroglycan and α-DG refer generally to these polypeptides from any species, and any allelic variants of such polypeptides. Preferably the species is human. Dystroglycan has been recently reviewed (Durbeej et al, Curr. Opin. Cell Biol., 10:594–601, 1998).

Genes Encoding α-DG Proteins

The present invention contemplates isolation of a gene encoding a dystroglycan or an α-DG of the invention, including a full length, or naturally occurring form of dystroglycan, and fragments thereof containing glycosylation sites, particularly the α-DG fragment.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a recombinant nucleic acid construct, such as plasmid, phage genome, virus genome, cosmid, or artificial chromosome, to which another DNA segment may be attached. In a specific embodiment, the vector may bring about the replication of the attached segment, e.g., in the case of a cloning vector. A "replicon" is any genetic element (e.g., plasmid, chromosome, virus) that functions as an autonomous unit of DNA replication in vivo, i.e., it is capable of replication under its own control.

A cell has been "transfected" by exogenous or heterologous DNA when such DNA has been introduced inside the cell. A cell has been "transformed" by exogenous or heterologous DNA when the transfected DNA is expressed and effects a function or phenotype on the cell in which it is expressed.

The present invention provides antisense nucleic acids (including ribozymes), which may be used to inhibit expression of α-DG of the invention. An "antisense nucleic acid" is a single stranded nucleic acid molecule which, on hybridizing with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

Specific examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heteroygloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine.

A "gene" is used herein to refer to a portion of a DNA molecule that includes a polypeptide coding sequence operatively associated with expression control sequences. In one embodiment, a gene can be a genomic or partial genomic sequence, in that it contains one or more introns. In another embodiment, the term gene refers to a cDNA molecule (i.e., the coding sequence lacking introns).

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA form eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

"Expression control sequences", e.g., transcriptional and translational control sequences, are regulatory sequences that flank a coding sequence, such as promoters, enhancers, suppressors, terminators, and the like, and that provide for the expression of a coding sequence in a host cell. In eukaryotic cells, polyadenylation signals are control sequences. On mRNA, a ribosome binding site is an expression control sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if it contains introns) and translated into the protein encoded by the coding sequence.

A "signal sequence" is included at the beginning of the coding sequence of a protein to be expressed on the surface or in the membrane of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences are found on the α-DG polypeptides of the invention, e.g., as exemplified infra.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their high degree of sequence similarity. This has been shown to be the case for dystroglycans from various species (Durbeej et al., supra).

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 85%, and most preferably at least about 90 or 95%, of the nucleotides match over the defined length of the DNA sequences. An example of such a sequence is an allelic variant of the specific α-DG genes of the invention. Sequences that are substantially homologous can be identified by comparing the sequences using standard software available in sequence data banks or from commercial sources (BLAST, DNA Strider, DNA Star, FASTA, etc.), or in a Southern hybridization experiment under, for example, stringent conditions as defined for that particular system. Defining appropriate hybridization conditions is within the skill of the art. See, e.g., Maniatis et al., supra: DNA Cloning, Vols. I & II, supra.

Similarly, in a particular embodiment, two amino acid sequences are "substantially homologous" or "substantially similar" when greater than about 80% of the amino acids are identical, or greater than about 85% are similar (functionally identical). Preferably, the similar or homologous sequences are identified by alignment using, for example, the GCG (Genetics Computer Group, Program Manual for the GCG Package, Version 7, Madison, Wis.) pileup program.

A gene encoding α-DG, whether genomic DNA or cDNA, can be isolated from any source, particularly from a human cDNA or genomic library. Methods for obtaining α-DG gene are well known in the art, as described above (see, e.g., Sambrook et al., 1989, supra). The DNA may be obtained by standard procedures known in the art from cloned DNA (e.g., a DNA "library"), and preferably is obtained from a cDNA library prepared from tissues with high level expression of the protein (e.g., a brain cell library, since these are the cells that evidence highest levels of expression of α-DG), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II).

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., E. coli, and facile purification for subsequent insertion into an appropriate expression cell line, if such is desired. For example, a shluttle vector, which is a vector that can replicate in more than one type of organism, can be prepared for replication in both E. coli and Saccharomyces cerevisiae by linking sequences from an E. coli plasmid with sequences from the yeast 2 m plasmid.

Expression of α-DG Polypeptides

The nucleotide sequence coding for α-DG, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Thus, the nucleic acid encoding α-DG of the invention is operationally associated with a promoter in an expression vector of the invention. Both cDNA and genomic sequences can be cloned and expressed under control of such regulatory sequences. An expression vector also preferably includes a replication origin.

Alternatively, an α-DG polypeptide of the invention can be isolated from cells that express the receptor endogenously, as described infra. It is also possible to prepare α-DG using well-known techniques in peptide synthesis, including solid phase synthesis (using, e.g., BOC of FMOC chemistry), or peptide condensation techniques.

As used herein, the terms "polypeptide" and "protein" may be used interchangably to refer to the gene product (or corresponding synthetic product) of an α-DG gene. The term "protein" may also refer specifically to the polypeptide as expressed in cells. A peptide is generally a fragment of a polypeptide, e.g., of about six or more amino acid residues.

Potential host-vector systems include but are not limited to mammalian cell systems infected with virus (e.g., vaccinia virus, adenovirus, adeno-associated virus, herpes virus, etc.), or with non-viral nucleic acid vectors (e.g., expression plasmids and the like); insect cell systems infected with virus (e.g., baculovirus). Bacterial expression systems can also be used, but these systems yield a non-glycosylated product, which does not interact with mycobacteria as shown in the examples, infra. The expression elements of vectors vary in their strengths and specificities. Depending on the host-vector system utilized, any one of a number of suitable transcription and translation elements may be used.

A preferred expression host is a eukaryotic cell (e.g., yeast, insect, or mammalian cell). More preferred is a mammalian cell, e.g., human, rat, monkey, dog, or hamster cell.

Expression of α-DG protein may be controlled by any promoter/enhancer element known in the art, but these regulatory elements must be functional in the host selected for expression. Promoters which may be used to control α-DG gene expression include, but are not limited to, cytomegalovirus (CMV) promoter, the SV40 early promoter region (Benoist and Chambon, 1981, Nature 290:304–310), the promoter contained in the 3' long terminal repeat of Rous sarcoma virus (Yamamoto, et al., Cell 22:787–797, 1980), the herpes thymidine kinase promoter (Wagner et al., Proc. Natl. Acad. Sci. U.S.A. 78:1441–1445, 1981), the regulatory sequences of the metallothionein gene (Brinster et al., Nature 296:39–42, 1982); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., J. Biol. Chem. 267:963–967, 1992 Wu and Wu, J. Biol. Chem. 263:14621–14624, 1988; Hartmut et al., Canadian Patent Application No. 2,012,311, filed Mar. 15, 1990).

In specific embodiments, α-DG can be obtained by expressing the dystroglycan gene, e.g., as described in Ibraghimov-Beskrovnaya et al. (Nature 355:696, 1992), or purifying the receptor from the cell membrane or peripheral nerve or skeletal muscle cells, e.g., as described in Yamada et al. (J. Biol. Chem. 271:23418, 1996; Yamada et al., FEBS Letters 352:49, 1994; and Ervasti et al., J. Biol. Chem. 266:9161, 1991).

To obtain α-DG through gene expression, a 4,200-nucleotide cDNA sequence that contains a 2685 nucleotide open reading frame coding for a polypeptide of 896 amino acids having a calculated $M_r$ of 97,029 is obtained. The 97K polypeptide is a precursor to α-DG (156K) and β-DG (43K, which is post-transationally modified to yield the two mature proteins. The N-terminal portion of the precursor 97K polypeptide is processed into the mature 156K α-DG having a putative core of about 56K. The 97K polypeptide may be cleaved by the endogenous protein processing pathway of eukaryotic cells to yield Cα-DG and β-DG. Several sites for attachment of N- and O-links carbohydrates are glycosylated to result in the mature 156K protein.

Transgenic Animals

In still another embodiment, various non-human (experimental) animals, such as mice, rabbits, rats, sheep, goats, cows, or dogs, can be made to express dystroglycan, and particularly α-DG, and more particularly, human α-DG. Such animals can provide valuable models for testing anti-leprosy drugs in vivo. Preferably, transgenic animals of the invention are receptive to productive *M. leprae* infection by virtue of expression of a human dystroglycan. Thus, in a preferred embodiment, the invention provides for a transgenic animal infected with *M. leprae*. The term infected is used herein to refer to a condition in which the mycobacteria are able to invade target cells, e.g., Schwann cells, and propagate. Such an infection may or may not lead to neurodegeneration or any of the pathological features of leprosy, to lepromatous module formation, or any other symptom found in leprosy. Preferably, however, one or more of these symptoms or features will be present in the animal.

Various techniques are known in the art to make transgenic animals. The animals can be created by insertion of the gene encoding dystroglycan into embryonic cells, so that the gene is inserted in a chromosome and becomes part of the genome. Alternatively, animals can be rendered transiently transgenic by delivering vectors carrying dystroglycan to cells, e.g., Schwann cells.

Genomic Transgenic Animals

In one embodiment, the invention provides a transgenic animal whose somatic and germline cells carry the human dystroglycan gene (see, e.g., Hogan et al., A Laboratory Manual, Cold Spring Harbor Laboratory, 1986).

Various transgenic animal models have been described (e.g., Coffman, Semin. Nephrol. 17:404, 1997; Esther et al., Lab. Invest. 74:953, 1996). Transgenic animal models have been used to study genetic neurodegenerative diseases (Price et al., Science:1079–83, 1998) and neurology and behavior (Picciotto and Wickman, Physiol Rev. 78:1131063, 1998). Transgenic animals are recognized as valuable for research and production of recombinant proteins (see, e.g., Heddle, Environ Mol Mutagen 32:110–4, 1998; Werner et al., Arzneimnittelforschung 48:870–80, 1998). Various patents have been issued that describe preparation of transgenic animals, including, but by no means limited to, U.S. Pat. Nos. 4,736,866 (Leder and Stewart); 4,870,009 (Evans et al.); 5,718,883 (Harlan and June); 5,614,396 (Bradley et al.); and 5,650,503 (Archibald et al.).

Transgenic Vectors

As discussed above, a vector is any means for the transfer of a nucleic acid according to the invention into a host cell. Preferred vectors for transient expression are viral vectors, such as retroviruses, herpes viruses, adenoviruses and adeno-associated viruses. Thus, a gene encoding a functional dystroglycan protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral Vectors. Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques 7:980–990, 1992). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., *Molec. Cell. Neurosci.* 2:320–330, 1991), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (*J. Clin. Invest.* 90:626–630, 1992; see also La Salle et al., *Science* 259:988–990, 1993); and a defective adeno-associated virus vector (Samulski et al., *J. Virol.* 61:3096–3101, 1987; Samulski et al., *J. Virol.* 63:3822–3828, 1989; Lebkowski et al., *Mol. Cell. Biol.* 8:3988–3996, 1988).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokies, such as interleukin-12 (IL-12), interferon-g (IFN-g), or anti-CD4 antibody, can be administered to block humoral or cellular immune responses to the viral vectors (see, e.g., Wilson, *Nature Medicine,* 1995). In addition, it is advantageous to employ a viral vector that is engineered to express a minimal number of antigens.

Non-viral vectors. Alternatively, the vector con be introduced in vivo by lipofection, as naked DNA, or with other transfection facilitating agents (peptides, polymers, etc.). For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Feigner, et. al., *Proc. Natl. Acad. Sci. U.S.A.* 84:7413–7417, 1987; see Mackey, et al., *Proc. Natl. Acad. Sci. U.S.A.* 85:8027–8031, 1988; Ulmer et al., *Science* 259:1745–1748, 1993). The use of cationic lipids may promote encapsulation of negatively charged nucleic acids, and also promote fusion with negatively charged cell membranes (Felgner and Ringold, *Science* 337:387–388, 1989). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear a that directing transfection to particular cell types would be particularly advantageous in a tissue with cellular heterogeneity, such as pancreas, liver, kidney, and the brain. Lipids may be chemically coupled to other molecules for the purpose of targeting (see Mackey, et. al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., *J. Biol. Chem.* 267:963–967, 1992; Wu and Wu, *J. Biol. Chem.* 263:14621–14624, 1988; Hartmut et al., Canadian Patent Application No. 2,012,311, filed Mar. 15, 1990; Williams et al., *Proc. Natl. Acad. Sci. USA* 88:2726–2730, 1991). Receptor-mediated DNA delivery approaches can also be used (Curiel et al., *Hum. Gene Ther.* 3:147–154, 1992; Wu and Wu, *J. Biol. Chem.* 262:4429–4432, 1987). U.S. Pat. No. 5,580,859 discloses delivery of exogenous DNA sequences, free of transfection facilitating agents, in a mammal.

The dystroglycan gene can be conveniently placed under control of a cellspecific or tissue-specific promoter to ensure expression in the desired cell type. Animal transcriptional control regions, which exhibit tissue specificity and have been utilized in transgenic animals, include: elastase I gene control region which is active in pancreatic acinar cells (Swift et al., 1984, Cell 38:639–646; Ornitz et al.) 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53-5), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalmus (Mason et al., 1986, Science 234:1372–1378).

Laminin

Laminin-2α, and particularly the G-domain of laminin-2α, has been found to be integral to the interaction between *M. leprae* and α-DG. Accordingly, the present invention contemplates the use of laminin-2, and particularly the G-domain of the laminin-2α chain (LNα2G), and particularly the portion thereof that includes both the mycobacterium and the α-DG binding sites in binding assays and the like. Alternatively, any molecule, including a fusion protein or synthetic construct, that contains the mycobacterium and α-DG binding regions of the G-domain of laminin-2α can be used in the practice of the invention. Accordingly, unless specifically indicated otherwise, reference herein to laminin-2α or the G-domain of laminin-2α in connection with the interaction of *M. leprae* with α-DG should be deemed to refer to any such molecule comprising the relevant binding region of the G-domain. Preferably, such a molecule is the G-domain of laminin-2α.

Laminin-2 or the binding portion thereof (e.g., the G-domain), can be isolated from natural sources or expressed recombinantly. The discussion of recombinant expression set forth above can be applied to the expression of laminin-2, or the G-domain of laminin-2. In a specific embodiment, infra, laminin-2 is expressed from a recombinant baculovirus expression system. However, any expression system, e.g., as described above, could be used as well.

Evaluation of the Degenerative Process

An important advantage of the present invention is the ability to evaluate and compare the neurodegenerative process associated with leprosy with muscular degeneration associated with muscular dystrophy. The rationale for this type of evaluation is the common involvement of dystroglycan.

Gene expression evaluation technologies, such as differential display and subtractive hybridization methods, can be used in the present invention to ascertain genes that are expressed or turned off as a consequence of *M. leprae*-LN-2 binding to α-DG. For example, in subtractive hybridization, cells expressing α-DG on their cell membranes are treated with *M. leprae*-LN-2, and mRNA transcribed as a result is isolated from cells. cDNA clones are generated from the mRNA. Common cDNA clones are selected out by hybridizing with control cells expressing the receptor only, leaving differentially expressed cDNA clones. Differential display and subtractive hybridization methods are more particularly described in U.S. Pat. Nos. 5,700,644, issued to Gould et al. and 5,665,547, issued to Pardee et al. The results of these techniques can be used to determine which genes are involved in uptake of *M. leprae* in Schwann cells. Furthermore, these techniques can be used with *M. teprae*-LN-2 to study gene expression regulation in muscle and nerve cells having characteristics of muscular dystrophy or peripheral neuropathies, i.e., diseases which exhibit loss or defect of laminin-2-α-dystroglycan interaction.

In a specific embodiment, oligonucleotide expression array technology can be used to evaluate gene expression after binding of mycobacteria to α-DG, and to identify gene expression that either correlates with or is distinct from gene expression in a muscular dystrophic disease (see, e.g., Little et al., Genet. Anal. 6:151, 1996). For example (and not by means of limitation), GeneChip expression analysis (Affymetrix, Santa Clara, Calif.) generates data for the assessment of gene expression profiles and other biological assays. Oligonucleotide expression arrays simultaneously and quantitatively interrogate thousands of mRNA transcripts (genes or ESTs), simplifying large genomic studies. Each transcript can be represented on a probe array by multiple probe pairs to differentiate among closely related members of gene families. Each probe cell contains millions of copies of a specific oligonucleotide probe, permitting the accurate and sensitive detection of low-intensity mRNA hybridization patterns. Differential expression data can provide a clear understanding of cellular pathways.

After hybridization intensity data is captured, e.g., using a Hewlett-Packard GeneArray™ scanner, software can be used to automatically calculate intensity values for each probe cell. Probe cell intensities can be used to calculate an average intensity for each gene, which directly correlates with mRNA abundance levels. Expression data can be quickly sorted on any analysis parameter and displayed in a variety of graphical formats for any selected subset of genes.

Other gene expression detection technologies include the research products manufactured and sold by Perkin-Elmer and Gene Logic, to name only two such companies.

Evaluation of Binding Carbohydrates on α-DG

In another embodiment, the present invention permits identification and characterization of the carbohydrate moiety on α-DG that binds to laminin. Such a carbohydrate, or carbohydrate attached to a peptide, can be used in place of the α-DG polypeptide as a competitive inhibitor of mycobacterium binding to target cells.

Various means are known in the art for isolating and characterizing carbohydrate groups. The glycosylation pattern, depending on protein structure, is influenced by the enzymatic system of the host cell as well as by fermentation conditions. Therefore, selection of host cells and culture conditions must take into account the requirement for a specific and stable glycosylation pattern. For the assessment of glycovariants, a number of protein analytical methods such as peptide mapping, isoelectric focusing, oligosaccharide mapping, MALDI-TOF (matrix assisted laser desorption mass spectrometry-time of flight), capillary electrophoresis and specific potency assays are available. Lectin binding assays can be conducted to establish the presence or absence of various carbohydrate groups. Alternative, endoglycosidase sensitivity can be used to identify or characterize the relevant carbohydrate groups. Site-specific mutation can be used to systematically delete glycosylation sites from α-DG, thus permitting identification of the sites that are involved in the interaction with *M. leprae*. Once these sites have been identified, various means can be adapted to isolate the carbohydrate present at that site, and to characterize its structure.

Naturally, the assays described above to modify the carbohydrate groups on α-DG can be used in conjunction with the binding/screening assays set forth below to evaluate whether the specific carbohydrate group is involved in the *M. leprae* interaction.

Evaluation of Binding Components of *M. leprae*

The present invention also provides for identifying components of *M. leprae* involved in the interaction with α-DG. For example, cell wall proteins or glycolipids from the mycobacterium can be isolated and tested for the ability to bind to α-DG in the presence of a molecule comprising at least the G-domain of laminin-2.

Screening Assays

In one embodiment, the invention provides a method for identifying inhibitors of *M. leprae*-LN-2-α-DG interaction, e.g., using high throughput screens. As used herein, a ligand is any molecule having an affinity for, and particularly the ability to bind to, another molecule. Such ligands can prevent the binding and uptake of *M. leprae* into its target cells, e.g., Schwann cells. Dystroglyan receptor may be expressed in eukaryotic cells as described above to develop and/or implement screening. The α-DG cDNA can be further employed to identify receptor subtype selective ligands, and to make chimeric and mutant α-DG for identifying critical binding domains thereof and selectivity of antagonists or agonists which disrupt binding of *M. leprae* and/or LN-2 to α-DG.

The expression screening systems can also be used to further investigate signal transduction systems of α-DG receptors and cellular responses to bacterial uptake after *M. leprae*-LN-2 binding, as described infra.

Alternatively, as demonstrated in the examples, the α-DG polypeptide (in glycosylated form) can be used in binding assays with *M. leprae*, e.g., in a solid phase binding assay.

In any of the screening assays, a molecule comprising the G-domain of the α-2 chain of laminin-2, including laminin-2, is used to mediate the interaction of *M. leprae* and α-DG. Furthermore, either the mycobacterium or the α-DG, or both, are generally labelled in a binding assay, or can be detected (e.g., using a secondary binding reagent such specific antibody), so that the presence or absence of binding can be determined. Various labelling systems are known in the art, and include without limitation fluorescent compounds, luminescent compounds, radioisotopes, latex particles, dyes, colloidal gold particles, and the like.

In another embodiment, screening assays for high throughput screens of molecules that up- or down-regulate cellular activity after *M. leprae*-LN-2 binds to α-DG, e.g., indicator cells specially engineered to indicate activity of a cell after *M. teprae* binds to α-DG via LN-2, are further contemplated by the invention. The gene expression technologies discussed above can be used to evaluate the consequences of mycobacterium binding, or the effect of test reagents on those consequences, which are believed to be mediated through the interaction with α-DG.

Accordingly, the present invention encompasses methods for identifying specific ligands for α-DG which block *M. leprae* adherence to cells using various screening assays known in the art. Furthermore, the invention permits identification of ligands that selectively bind α-DG via LN-2 in a manner similar to *M. leprae*.

Any screening technique known in the art can be used to screen for agonists or antagonists of *M. leprae*-α-DG interaction. The present invention contemplates screens for small molecule ligands or ligand analogs and mimics, and screens for natural ligands that bind to and agonize or antagonize the binding of *M. leprae* to α-DG. For example, natural product libraries can be screened using assays of the invention. Generally, compounds are tested for the ability to compete with labeled *M. leprae*-LN-α2G for binding to the α-DG receptor.

Knowledge of the primary sequence of the binding regions on α-DG and LN-α2G, and the similarity of that sequence with proteins of known function, can provide clues as to inhibitors of *M. leprae*-LN-α2G binding to α-DG. Identification and screening of antagonists or agonists is further facilitated by determining structural features of binding regions, e.g., using X-ray crystallography, neutron diffraction, nuclear magnetic resonance spectrometry, and other techniques for structure determination. These techniques provide for the rational design or identification of agonists and antagonists.

A second approach uses primarily chemical methods, of which the Geysen method (Geysen et al., Molecular Immunology 23:709–715, 1986; Geysen et al. J. Immunologic Method 102:259–274, 1987) and the method of Fodor et al. (Science 251:767–773, 1991) are examples. Furka et al. (14th International Congress of Biochemistry, Volume #5, Abstract FR:013, 1988; Furka, Int. J. Peptide Protein Res. 37:487–493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., Proc. Natl. Acad. Sci. USA 90:10700–4, 1993; Ohlmeyer et al., Proc. Natl. Acad. Sci. USA 90:10922–10926, 1993; Lam et al., International Patent Publication No. WO 92/00252; Kocis et al., International Patent Publication No. WO 9428028) and the like, can be used to screen for ligands that effect the binding of *M. leprae*-LN-α2G to α-DG.

The screening can be performed with recombinant cells that express the α-DG, or alternatively, using purified receptor, e.g., produced recombinantly, as described supra. For example, the ability of labeled, goluble or golubilized α-DG that includes the ligand-binding (*M. leprae*-LN-α2G) portion of the receptor, to bind ligand can be used to screen libraries, as described in the foregoing references. In a specific embodiment, infra, cell membranes containing recombinantly produced α-DG can be used in binding assays with various ligands.

Calcium Influx Assay

Whole cells expressing the α-DG receptor are loaded with a fluorescent dye that chelates calcium ions, such as FURA-2. Upon addition of *M. leprae*-LN-α2G to these cells, binding to α-DG receptors causes calcium flux. The dye chelates these calcium ions. Spectrophotometric determination of the ratio for dye:calcium complexes to free dye determine the changes in intracellular calcium concentrations upon addition of *M. leprae* -LN-α2G. Hits from screens and other test compounds can be similarly tested in this assay to functionally characterize them as agonists or antagonists. Increases in intracellular calcium concentrations are expected for compounds with agonist activity while compounds with antagonist activity are expected to block *M. leprae*-LN-α2G stimulated increases in intracellular calcium concentrations.

Therapeutic Implications

The present invention provides various reagents and methods for inhibiting *M. leprae* uptake into cells by interfering with the interaction of the mycobacterium with α-DG. As shown in the examples, infra, free α-DG (in soluble form, not associated with β-DG) can be used to inhibit mycobacterium binding with target cells (Schwann cells). It is further contemplated that the carbohydrate group on α-DG that binds to laminin can be used, either alone or conjugated to a peptide, to inhibit mycobacterium binding to target cells. Thus, the present invention includes methods and pharmaceutical compositions designed to effect these outcomes.

In a specific embodiment, the invention provides an inhibitor of the interaction between mycobacterium and α-DG, in an admixture with a pharmaceutically acceptable excipient. The phrase "pharmaceutically acceptable" refers to molecular entities and compositions that arc physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly mn humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The invention further relates to a method for inhibiting uptake of mycobacterium by target cells, comprising administering an amount of an inhibitor of binding of mycobacterium to α-DG effective to inhibit such binding (i.e., an inhibitory amount). In a preferred embodiment, inhibition can have a therapeutic outcome. In other words, the inhibitor can be administered to a subject who is suspected of suffering from an infection of *M. leprae*, in a therapeutically effective amount. The phrase "therapeutically effective amount" is used herein to mean an amount sufficient to reduce by at least about 15 percent, preferably by at last 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

In a specific embodiment, the inhibitor is a soluble α-DG polypeptide (in glycosylated form). The soluble α-DG can be administered directly to the subject, or can be expressed from a vector comprising a coding sequence for soluble α-DG (such vectors encoding soluble α-DG are discussed above; gene delivery vectors are described in detail in connection with "Trangenic Vector," above). In another embodiment, the inhibitor is a dystroglycan antisense nucleic acid, which inhibits the expression of α-DG.

The present invention will be more fully explained by reference to the following examples, which are intended to be illustrative and not limiting thereof.

EXAMPLE 1

Figure 1B:
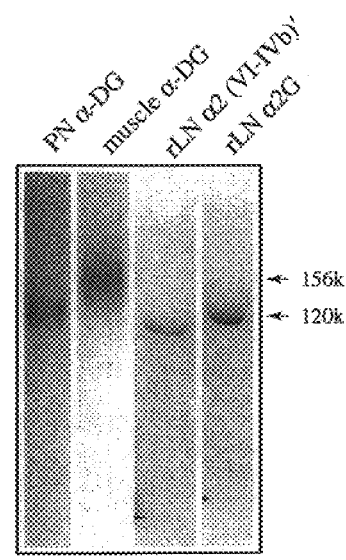

This Example demonstrates the role of α-dystroglycan in *M. leprae* bacterial interaction with Schwann cells. Binding of *M. leprae* to native α-dystroglycan purified from bovine peripheral nerves and rabbit skeletal muscle was examined in the presence or absence of recombinant fragments of the laminin-α2 chain (FIGS. 1A and 1B).

Methods

Mycolgacterim. *M. leprae* was obtained from the laboratory of Dr. Patrick Brennen of the Colorado State University, which is funded by the NIH specifically to provide *M. leprae* to other laboratories. Each bacterial isolate was tested for acid-fast labeling and *M. leprae*-specific phenolic glycolipid-1 (PGL-1) reactivity using auramine-rhodamine Bacto TB Fluorescent Stain Kit (Difco, Detroit, Mich.) and MAb to native PGL-1, respectively, prior to assays.

Purification of α-DG. Purification of bovine peripheral nerve α-dystroglycan was performed as described in Yamada et al., J. Biol. Chem. 271:23418, 1996; Yamada et al., FEBS Letters 352:49, 1994; Ervasti et al., J. Biol. Chem. 266:9161, 1991. Rabbit skeletal muscle α-dystroglycan was purified employing the same method but using KCl-washed heavy microsomes of rabbit skeletal muscle as a starting material. α-Dystroglycan fusion proteins B and D (FP-B and FP-D) were prepared as described in Ibraghimov-Beskrovnaya et al., Nature 355:696, 1992 Campbell, Cell 80:675, 1995. Two segments corresponding to the α-dystroglycan core protein, except amino acid residues 30–61, were expressed as glutathione S-transferase (GST) fusion proteins using pGEX vectors in *E. coli*. Fusion protein-D (FP-D) contains amino acid residues 62–438, corresponding to the N-terminal region of the 97K precursor dystroglycan polypeptide. Fusion protein-B (FP-B) contains amino acid residues 367–863, corresponding to a portion of the N-terminal region of the 97K precursor. The predicted signal sequence was contained in amino acid residues 1–29.

Recombinant Laminin. Recombinant (r) LN-α2G, rLN-α2(VI-IVb)' and rLN-α1G fragments were prepared using a baculovirus expression system as previously described (Rambukkana et al., Cell 88:811–821, 1997; Yurchenco et al., J. Biol. Chem. 268:8356, 1993). Human merosin (laminin-2/4) was obtained from Gibco-BRL (Gaithersburg, Md.).

The purity of dystroglycan preparations and recombinant fragments of laminins was analyzed by SDS-PAGE and immunoblotting using antibodies specific for each fraction as described (Rambukkana et al., supra).

Binding Assay. *M. leprae* binding to α-dystroglycan was determined by a solid phase bacterial adherence assay as described in Rambukkana et al., supra. Fifty µg/ml of immobilized native α-dystroglycan purified from peripheral nerves or skeletal muscles or 50 mg/ml of recombinant α-dystroglycan were overlaid with recombinant fragments of the laminin-α2 chain (prepared as described supra), Terasaki plates were coated overnight with 50 µg/ml (0.5 µg per well) α-dystroglycan or bovine serum albumin (BSA) as negative controls, *M. leprae* (5α108 bacteria/ml) suspension was preincubated with 10 µg/ml (0.1 µg per well) rLNα2G or LNα2(VI-IVb)' or BSA for 1 h at 37° C. After blocking the nonspecific binding with BSA, 10 µl of the *M. leprae* mixture was added to each well and incubated for 1 h at 37° C. Unbound bacteria were removed by washing with DPBS and wells were fixed with 2.5% glutaraldehyde (Sigma). Adherent *M. leprae* was detected by acid-fast labeling, counted, and expressed as described (Rambukkana et al., supra). The effect of heparin and EDTA on rLNα2G-mediated *M. leprae* binding to adystroglycan was determined similarly by incubating the bacterial mixture with 10 mM EDTA or 1 mg/ml heparin. Effect of periodate treatment was evaluated by preincubation of increasing concentrations of sodium periodate with native immobilized α-dystroglycan prior to the addition of rLNα2G +*M. leprae*. The number of adherent *M. leprae* (ML) within a 0.25 mm$^2$ grid area of each well was quantified after 60 min of incubation, and the data were expressed as the mean ±SD values from 5–6 wells (FIG. 1A). Three additional experiments were conducted giving similar results.

Coomassie blue stained SDS-PAGE was performed according to standard protocol, to determine the role of α-DG in *M. leprae* adherence to Schwann cells. Native α-dystroglycan preparations and recombinant laminin-α2 chain fragments are used in the present Example (peripheral nerve α-dystroglyean (PNα-DG; 120-kD), muscle α-dystroglycan (muscle α-DG; 156-kD), rLN-α2 (VI-IV)' (116-kD) and rLN-α2G (120-kD) (FIG. 1B).

Results

In the solid phase assay, *M. leprae* bound to immobilized α-dystroglycan only in the presence of the COOH-terminal fragment of the laminin-α2 chain (rLNα2G; FIG. 1A). *M. leprae* also bound to muscle α-dystroglycan only in the presence of rLN-α2G (FIG. 1A). *M. leprae* binding to α-dystroglycan of both peripheral nerve and muscle was increased by more than 95% with 10 µg/ml (0.1 µg per well) of rLNα2G. Even higher concentrations (100 µg/ml) of the NH2-terminal r(VI-IVb)' fragment of laminin-α2 chain or the G domain of the laminin-α1 chain (rLNα1G) had no effect on *M. leprae* binding to α-dystroglycan (110±24 and 130±31 bacteria per 0.25 mm$^2$ respectively), suggesting that the G domain of the laminin-α2 chain specifically mediated *M. leprae* binding to α-dystroglycan. Thus, LNα2G has two binding sites, one for *M. leprae* and the other for α-dystroglycan, and the G domain forms a bridge between *M. leprae* and α-dystroglycan. Additionally, the activity of total merosin or α2 laminins (a mixture of laminin-2 and 4) on *M. leprae*-α-dystroglycan interaction yielded results similar to rLNα2G at equal molar ratio (1010±110 and 1290±161 bacteria per 0.25 mm$^2$ respectively).

Figure 2A:
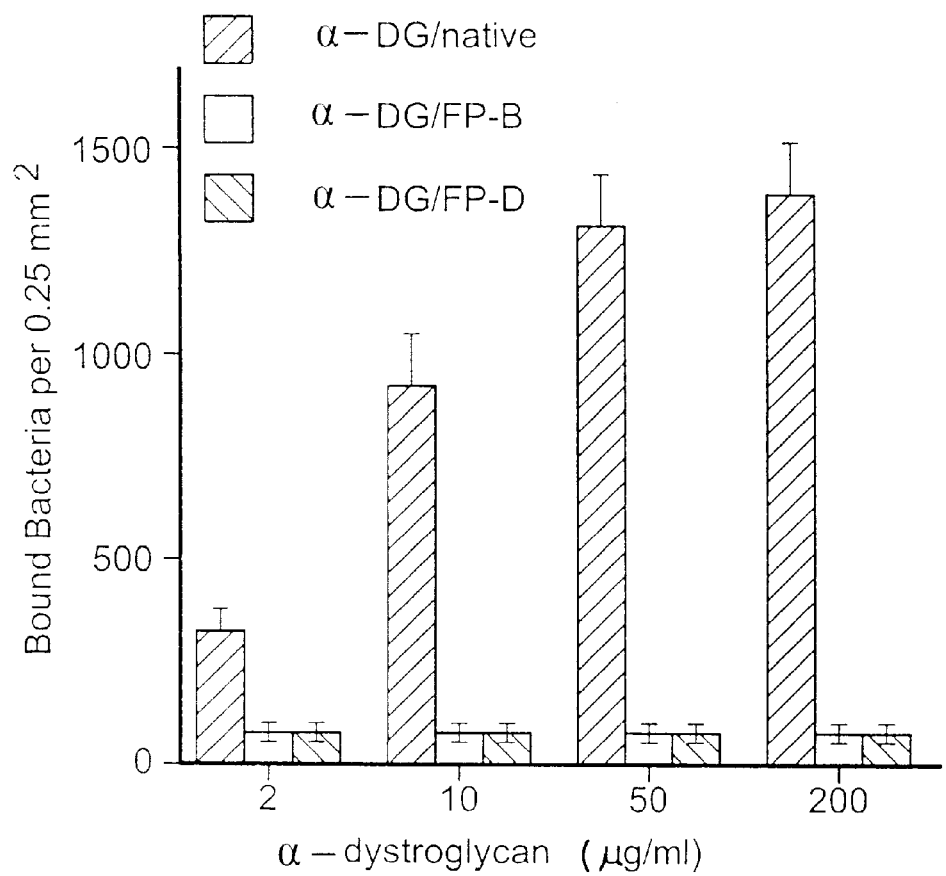
FIGS. 2A, 2B, 2C, 2D, and 2E. Characteristics of rLN-α2G-mediated M. leprae binding to α-dystroglycan. (A) Schematic diagram showing M. leprae adherence to increasing concentrations of native peripheral nerve α-dystroglycan and fusion proteins FP-B and FP-D of human dystroglycan in the presence of 10 μg/ml of human rLN-α2G. M. leprae binding to α-dystroglycan were expressed by subtracting the values of M. leprae +rLN-α2G binding from M. leprae+ BSA binding. Data shown are the means and standard error of triplicates of M. leprae adherence at each concentration of dystroglycan from a repreentative experiment (two additional experiments gave similar results). (B) Schematic diagram showing the fusion proteins (FP) of α-dystroglycan used in this study. (C) Coomassie blue stained SDS-PAGE gel showing the purified FP-D (left) and FP-B (right). (D) Effect of sodium periodate treatment on rLN-α2G-mediated M. leprae binding to α-dystroglycan. (E) rLN-α2G-mediated M. leprae binding to α-dystroglycan (50 μg/ml) in the presence of 10 mM EDTA and 1 mg/ml heparin. Data shown are mean and standard error from three experiments.
Figure 2B:
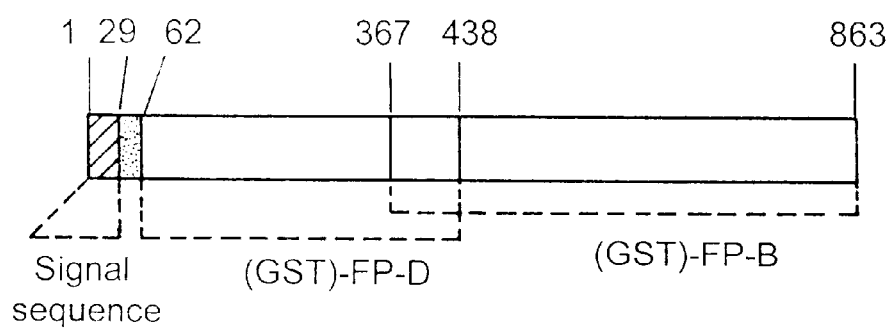
Figure 2C:
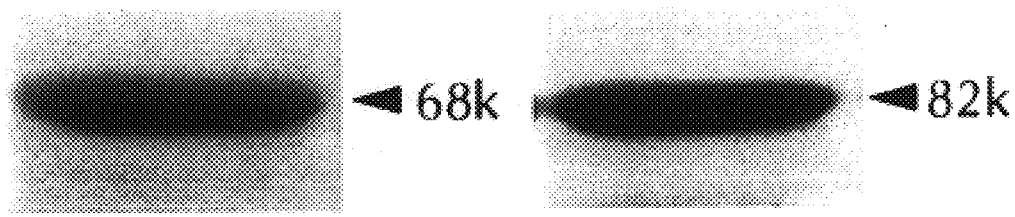
Figure 2D:
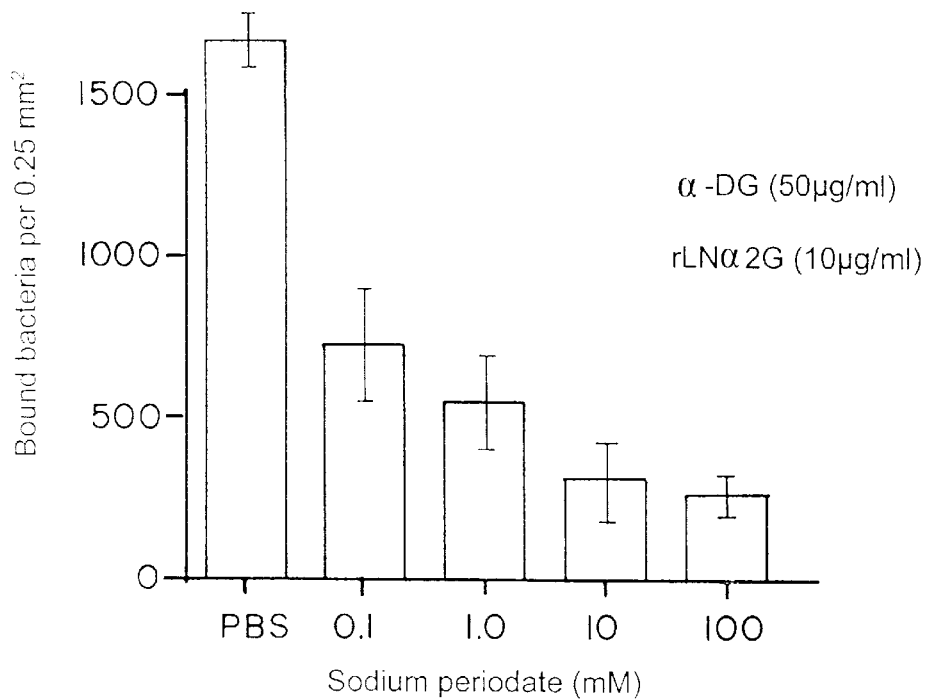

Comparison of rLNα2G-mediated *M. leprae* binding to native (FIG. 1B) versus fusion proteins of α-dystroglycan (FIG. 2B, C), showed that the bacteria strongly bound only to the native α-dystroglycan in a concentration-dependent manner (FIG. 2A). Glycosylation is the most likely post-translational modification contributing to the adystroglycan interaction with *M. leprae* via LN-α2G domain, because the native conformation of α-dystroglycan appeared unnecessary for laminin interaction. It has been reported that denatured dystroglycan also binds laminins (Ervasti and Campbell, J. Cell. Biol. 122:809, 1993; Suzuki et al., Eur. J. Biochem. 220:283, 1994; Yamada et al., J. Neurochem 66:1518, 1996; Yang et al., J. Biol. Chem. 270:11711, 1995 and to M. leprae+rLNα2G (data not shown).

rLNα2G-mediated M. leprae binding to α-dystroglycan was sensitive to periodate (FIG. 2D). Sodium periodate as low as 0.1 mM resulted in significant decrease (greater than 50%) of binding whereas 10 mM periodate dramatically reduced binding (greater than 80%). Thus, the carbohydrate moieties of α-dystroglycan are likely important for rLNα2G-mediated M. leprae interactions. Periodate and EDTA treatment did not detach the α-dystroglycan from wells, as no difference was found in antibody activity to α-dystroglycan before and after treatment as detected by ELISA using polyclonal antibodies to α-dystroglycan.

α-Dystroglycans are differentially glycosylated in different tissues of the same species (e.g., peripheral nerve versus muscle), which contributes to different molecular sizes of α-dygtroglycan (Ervasti et al., J. Biol, Chem 272:22315, 1997) (FIG. 1B) glycosylation of α-dystroglycan is nearly identical across species for particular tissues (e.g., peripheral nerve). Thus, the glycosylation is almost identical in peripheral nerve from mouse, rabbit, cow and human (Campbell, 1995, supra: Ervagti, supra; Ibraghimov-Beskrovnaya, supra; Chiba et al., J. Biol. Chem 272:2156, 1997).

Figure 2E:
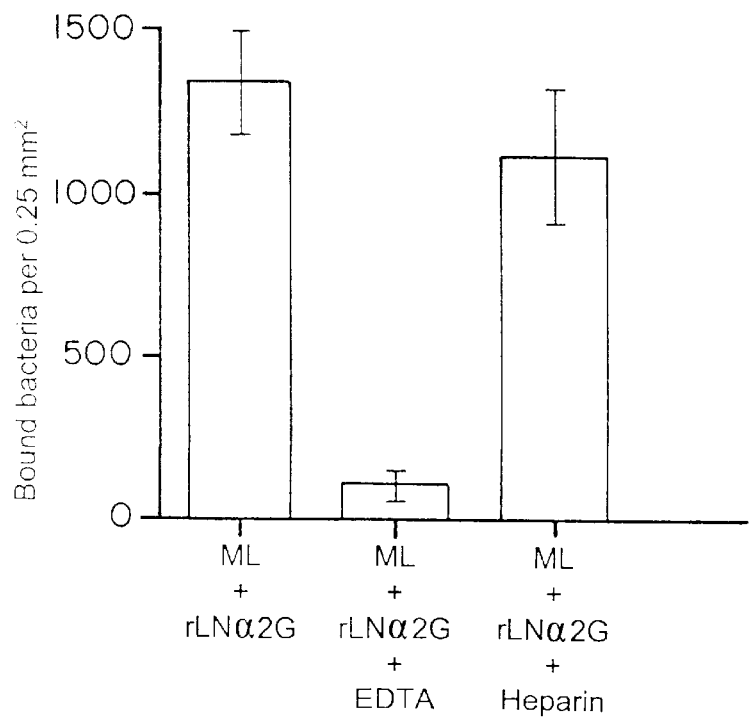

Further characterization of the rLNα2G-mediated M. leprae-α-dystroglycan interaction showed that this binding is completely abolished by EDTA, indicating the crucial role of calcium for the interaction of the G domain with α-dystroglycan. Moreover, the lack of inhibitory effects of heparin on rLNα2G-mediated M. leprae binding to α-dystroglycan (FIG. 2E) suggests that the heparin binding site of the G domain of the laminin-2 molecule is different from the α-dystroglycan binding site. Thus, the G domain is the α-dystroglycan binding site of the laminin-2 molecule, and this interaction is dependent on calcium and largely mediated by the carbohydrate moieties of α-dystroglycan. This finding may be of significant physiological relevance in muscular dystrophies because the loss of laminin-2 interaction with α-dystroglycan is critical for the pathogenesis of this disease (Campbell, 1995, supra; Ervasti and Campbell, supra; Yang et al., J. Biol. Chem. 270:11711, 1995).

EXAMPLE 2

This Example determined that peripheral nerve α-dystroglycan serves as a Schwann cell receptor for M. leprae.

Methods

Isolation of Schwann cells. Schwann cells were isolated from neonatal rat sciatic nerve, purified and amplified as described (Einheber et al., Cell Biol. 123:1223, 1993). Human Schwann cells were purified and immortalized as described (Rutkowski et al., in Neoplastic Transformation in Human Cell Systems In Vitro, J. S. Rhim and A. Dripschillo, Eds., Humana Press, Totowa, N.J., 1991, pp. 343–346). Isolated cells were plated onto poly-L-lysine-coated eight-well Lab-Tek chamber slides (Nunc) or 12 mm coverslips and cultured without forskolin to prevent the deposition of laminin-2. Purified Schwann cells grown for 3 days without forskolin were inoculated with M. leprae which were preincubated with 10 μg/ml either rLN-α2G or BSA. The number of M. leprae bound Schwann cells were expressed per 100 cells and data were presented as mean±SD from three separate experiments.

Binding Assays. For competitive inhibition assays, rLNα2G-coated M. leprae were preincubated with increasing concentrations of native α-dystroglycan for 3 hours at 37° C., after which the mixture was added to Schwann cells and the adherence assays were performed as described supra. Cell bound M. leprae were detected by acid-fast labeling and values are presented as percent binding of control (mean±SD) obtained from three different experiments. Net rLN-α2G-mediated M. leprae adherence to Schwann cells [(M. leprae+rLN-α2G)-(M. leprae+BSA)] in the absence of α-dystroglycan was considered as 100% binding. The number of acid-fast labeled bacteria were quantified and values were presented as the mean percent binding of controls. Net rLNα2G-mediated M. leprae adherence to Schwann cells were considered as 100%.

Results

Figure 3A:
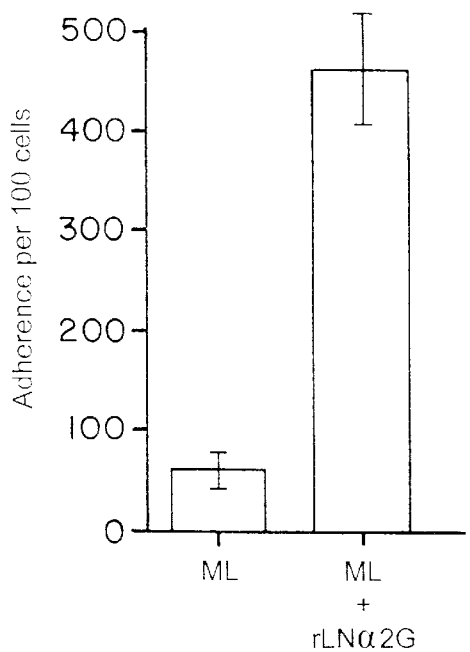
FIGS. 3A, 3B, 3C, 3D, 3E and 3F. α-Dystroglycan involvement in rLNα2G-mediated M. leprae adherence to Schwann cells. (A) M. leprae adherence to primary rat Schwann cells in the presence or the absence of rLN-α2G. (B) Competitive inhibition of rLN-α2G-mediated M. leprae binding to primary rat Schwann cells by native peripheral nerve α-dystroglycan. (C) α-Dystroglycan expression on primary Schwann cells purified from rat sciatic nerve as shown by immunofluorescence labeling by anti-α-dystroglyean MAb IIH6. (D) M. leprae adherence to human Schwann cells in the presence or the absence of rLN-α2G under similar conditions as in (A). (E) Competitive inhibition of rLN-α2G-mediated M. leprae binding to human Schwann cells by native α-dystroglycan under similar conditions as in (B). (F) α-Dystroglycan expression on immortalized human Schwann cells as detected by immunofluorescence using anti-α-dystroglycan MAb IIH6.

Primary rat Schwann cells and immortalized human Schwann cells were used for both adherence and invasion assays. These cells are devoid of LNα-2G permitting external control of binding. Primary rat and immortalized human Schwann cells were found to be 100% pure as determined by anti-S100 antibody. The cells strongly expressed α-dystroglycan but showed almost no deposition of LNα2G in early cultures (FIG. 3C; 21); they were also devoid of certain laminin receptors, e.g., the integrin β4 subunit. Exogenous rLNα2G efficiently mediated M. leprae adherence to primary Schwann cells (FIG. 3A). Since it was previously determined that M. leprae binds to rLNα2G with high affinity (Rambukkana et al, supra), the combination of these findings provides a model system to study of the involvement of α-dystroglycan in G domain-mediated M. leprae-Schwann cell interactions independent of the influence of other regions of the laminin-2 molecule.

Figure 3B:
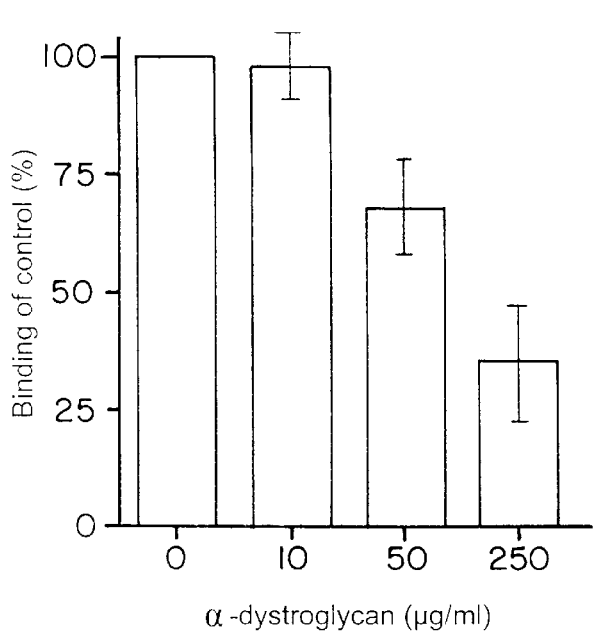

Using this system in competition assays, the rLNα2G-mediated M. leprae binding to Schwann cells was inhibited by preincubation of the M. leprae+rLNα2G complex with native α-dystroglycan in solution (median inhibitory concentration, $IC_{50}$=160 μg/ml) (FIG. 3B). Fusion proteins of α-dystroglycan (lacking carbohydrates) had no inhibitory effect on M. leprae binding to Schwann cells (data not shown). Thus, it is likely that the carbohydrate moeities of α-dystroglycan are involved in G domain-mediated M. leprae interaction with Schwann cells.

Figure 3D:
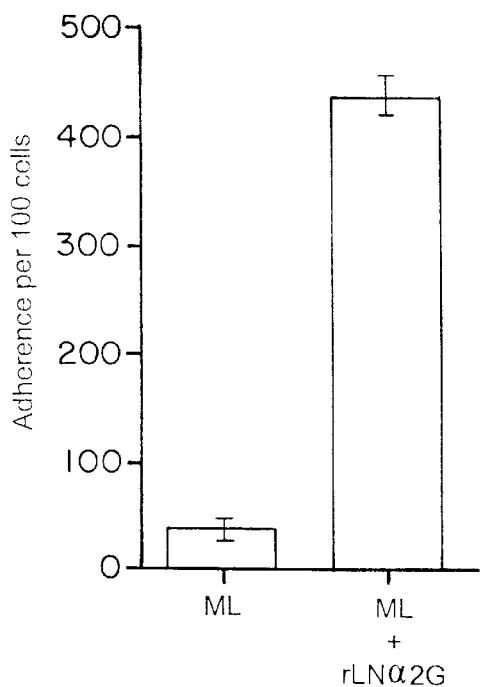
Figure 3E:
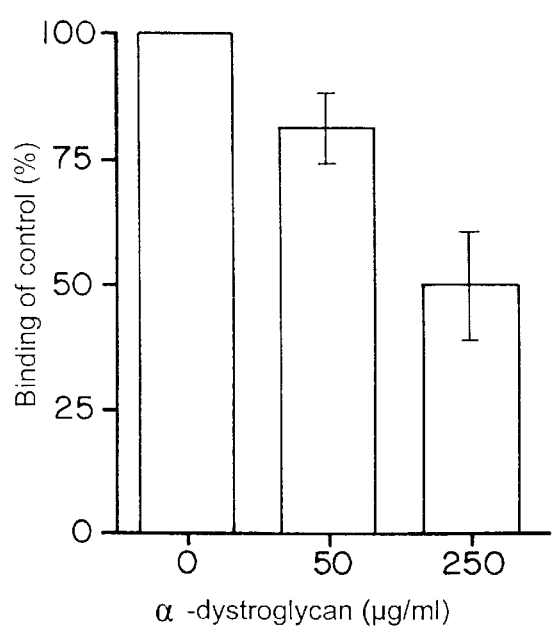
Figure 3C:
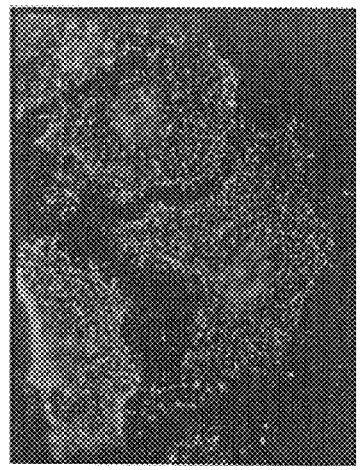
Figure 3F:
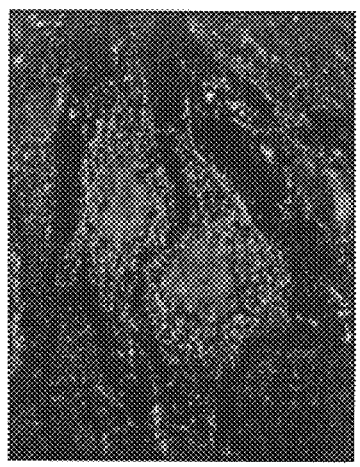

Monoclonal antibody (MAb) IIH6 (Campbell, Cell 80:675, 1995), which is specific for α-dystroglycan, strongly reacted with human Schwann cells (FIG. 3F). The pattern of α-dystroglycan expression on the dorsal surface of the live cells was in the form of microclusters, which was also found for primary rat Schwann cells (FIGS. 3C and 3F). While M. leprae alone showed almost no binding to human Schwann cells, preincubation of M. leprae with 10 μg/ml of rLNα2G resulted in a >90% increase of cellular adherence (FIG. 3D). This binding was inhibited by preincubation of the M. leprae+rLNα2G complex with native α-dystroglycan (median inhibitory concentration, $IC_{50}$=250 μg/ml; FIG. 3E). The low inhibitory effect of α-dystroglycan on M. leprae+rLNα2G binding to human Schwann cells, as compared with primary rat Schwann cells (FIG. 3B), may be due to the increased expression of other molecules (e.g., secretory products) on the transformed human Schwann cells, which mask the inhibitory effect of native α-dystroglycan. Nevertheless, both rat and human Schwann cell α-dystroglycan are involved in LNα2G-mediated M. leprae adherence to Schwann cells. Purified α-dystroglycan was unable to compete 100% for rLNα2G-mediated M. leprae adherence, suggesting the possibility of the involvement of other Schwann cell laminin receptors in bacterial adherence.

EXAMPLE 3

This Example further substantiates the involvement of α-dystroglycan as a Schwann cell receptor for *M. leprae*, by showing the effect of rLNα2G-coated *M. leprae* challenge on the distribution of α-dystroglycan receptors on live primary Schwann cells.

Methods

Light microscopy and immunofluorescence of Schwann cells were performed as described (Rambukkan et al, supra). Characterization of MAb IIH6 against α-dystroglycan and affinity purified rabbit PAb to human rLN-α2G are described in Examples 1 and 2. α-Dystroglycan detection and clustering studies were performed as previously reported (Cohen et al., J. Cell Biol. 136:1047–58, 1997). For bacterial-induced α-dystroglycan clustering, *M. leprae* was preincubated with rLN-α2G for 1 h at 37° C., the mixture was centrifuged, and the pellet was resuspended in PBS in order to avoid the contact of free rLN-α2G with Schwann cells. These rLN-α2G-coated *M. leprae* were added onto primary Schwann cells as described in adhesion assays in Example 1. Cultures were then stained live and fixed with 2.5% glutaraldehyde before processing for fluorescence microscopy. In live Schwann cells, α-dystroglycan labeling is restricted to the dorsal surface as IIH6 IgM MAb is unable to reach the ventral cell surface due to its large size. Co-localization of α-dystroglycan and *M.leprae* was performed by double immunofluorescence using MAb IIH6 and MAb to *M. leprae* PGL-1.

Figure 4A:
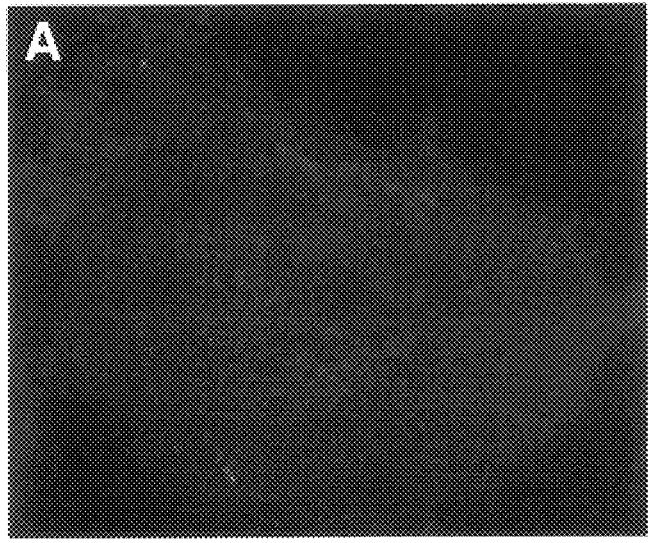
FIGS. 4A, 4B, 4C, and 4D. α-Dystroglycan receptor clustering on Schwann cells induced by rLN-α2G-coated M. leprae. (A) Immunofluorescence of α-dystroglycan showing its distribution on the dorsal surface of live primary Schwann cells before bacterial challenge. The areas corresponding to the nuclei of cells are out of focus. (B, C) Representative examples showing different forms of macroclusters of α-dystroglycan after three hours of bacterial challenge. Comparison of (A) vs (B and C) shows that rLN-α2G-coated M. leprae induced an extensive aggregation of α-dystroglycan receptors on the dorsal surface of Schwann cells. (C) and (D) Co-localization of α-dystroglycan receptor clusters and M. leprae on the same Schwann cell as detected by immunodouble labeling using MAbs to α-dystroglycan (IIH6) (C) and M. leprae specific PGL-1 (D). The arrows mark the α-dystroglycan clustering site approximately corresponding with Schwann cell-bound M. leprae. All labeling was visualized using 100× oil immersion objective.

Results

α-Dystroglycan is a mobile receptor on muscle cells and forms clusters when it interacts with matrix proteins. In control primary Schwann cell cultures, α-dystroglycan labeling, as determined by MAb IIH6, was equally distributed as microclusters on the dorsal surface of live Schwann cells (immunolabeled as individual dots; FIG. 4A). Microclusters (each dot) on unstimulated Schwann cells may represent single α-dystroglycan molecules, as was suggested previously for muscle cells (Cohen et al., J. Cell Biol. 136, 1047 (1997)).

Figure 4B:
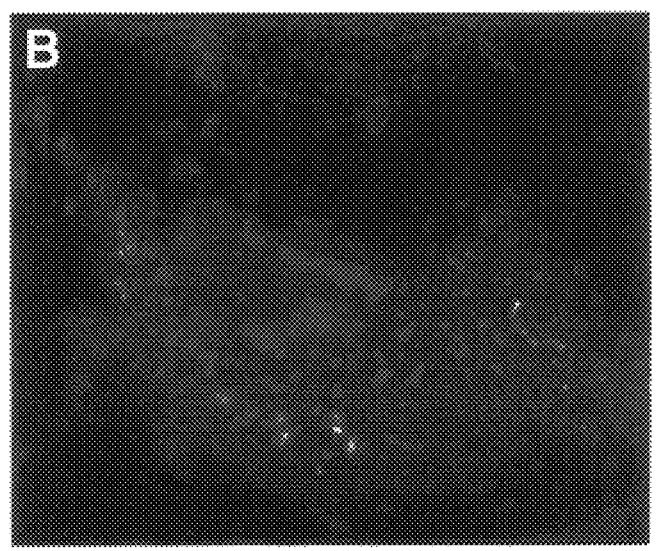
Figure 4C:
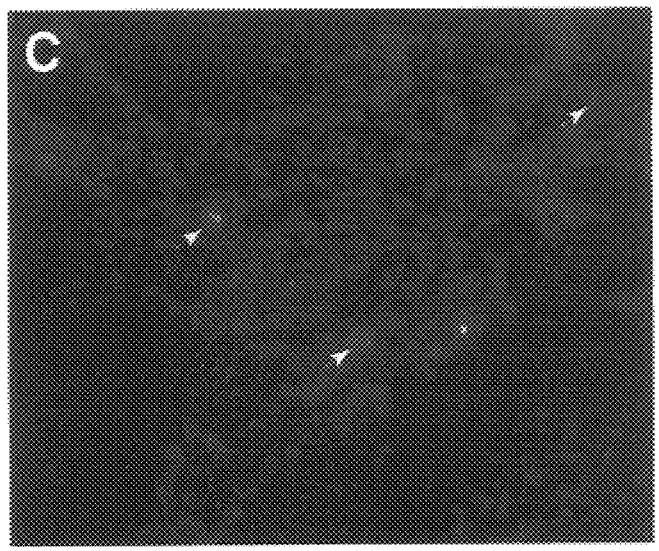
Figure 4D:
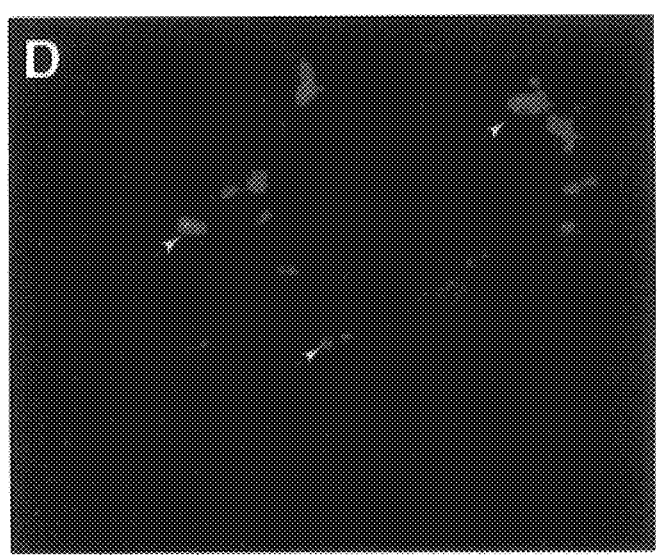

When Schwann cells were challenged with rLNα2G-coated *M. leprae* (after removing free rLNα2G), α-dygtroglycan labeling on most of the Schwann cells appeared as aggregates or macroclusters with different sizes and shapes over the entire dorsal cell surface (FIG. 4B and C). Bacterial challenge caused a dramatic decrease of microclusters and increased the number of macroclusters (compare FIG. 4A with FIGS. 4B and 4C) which suggest that macroclusters were derived from microclusters. FIGS. 4C and 4D demonstrate the co-localization of α-dystroglycan receptor clusters and *M. leprae* on the same Schwann cell. Because *M. leprae* alone failed to induce cluster formation (data not shown), the clustering of α-dystroglycan on Schwann cells appeared to be contributed by the *M. leprae* bound LNα2G. These data strongly suggest that α-dystroglycan participates in the LNα2G-mediated *M. leprae* interaction with Schwann cells, and that this binding results in receptor clustering.

All patents, publications, applications, and test methods mentioned above are hereby incorporated by reference.

Many variations of the present invention will suggest themselves to those skilled in the art in light of the above, detailed description. All such obvious variations are within the patented scope of the appended claims.

What is claimed is:

1. A method for identifying compounds that inhibit laminin-α2G mediated binding of *Mycobacterium leprae* to an isolated α-dystroglycan polypeptide, which method comprises incubating *Mycobacterium leprae*, the α-dystroglycan polypeptide and a molecule comprising a laminin-α2G domain with a compound suspected of having inhibitory activity under conditions that allow for laminin-α2G mediated binding of *Mycobacterium leprae* to the isolated α-dystroglycan polypeptide; and determining the presence or absence of a laminin-α2G/ *Mycobacterium leprae* complex bound to the isolated α-dystroglycan polypeptide;

wherein the absence of the laminin-α2G/*Mycobacterium leprae* complex bound to the isolated α-dystroglycan polypeptide is indicative of a compound that inhibits said binding.

2. The method according to claim 1, wherein the α-dystroglycan polypeptide is labeled.

3. The method according to claim 1 wherein the *Mycobacterium leprae* is labeled.

4. The method according to claim 1, wherein the compound is a cellular component of *Mycobacterium leprae*.

5. The method according to claim 1 wherein the compound comprises a carbohydrate from α-dystroglycan.

6. A method for identifying an isolated cellular component of *Mycobacterium leprae* that binds to α-dystroglycan via interaction with laminin-α2G, which method comprises incubating the isolated cellular component of *Mycobacterium leprae* and laminin-α2G under conditions that allow for the formation of a laminin-α2G/ *Mycobacterium leprae* complex;

incubating the laminin-α2G/*Mycobacterium leprae* complex with α-dystroglycan under conditions that allow for the complex to bind to α-dystroglycan; and determining the presence or absence of a laminin-α2G/ *Mycobacterium leprae* complex bound to the α-dystroglycan;

wherein the presence of the laminin-α2G/*Mycobacterium leprae* complex bound to the α-dystroglycan is indicative of an isolated cellular component of *Mycobaterium leprae* that binds to α-dystroglycan via interaction with laminin-α2G.

7. The method according to claim 2, wherein the *Mycobacterium leprae* component is labeled.

8. The method according to claim 2 wherein the α-dystroglycan is from a cell other than a Schwann cell.

* * * * *